(12) United States Patent
Yoshioka et al.

(10) Patent No.: US 8,390,281 B2
(45) Date of Patent: Mar. 5, 2013

(54) WIRE ROPE FLAW DETECTOR FOR INCREASING ACCURACY INDEPENDENT OF SPEED WHILE CONSERVING DETECTOR SIZE

(75) Inventors: Takashi Yoshioka, Tokyo (JP); Hiroshi Sasai, Tokyo (JP); Koichiro Nishiyori, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 146 days.

(21) Appl. No.: 12/866,847

(22) PCT Filed: Apr. 14, 2008

(86) PCT No.: PCT/JP2008/057256
§ 371 (c)(1),
(2), (4) Date: Aug. 9, 2010

(87) PCT Pub. No.: WO2009/128127
PCT Pub. Date: Oct. 22, 2009

(65) Prior Publication Data
US 2011/0006762 A1    Jan. 13, 2011

(51) Int. Cl.
*G01N 27/82* (2006.01)
(52) U.S. Cl. ........................ 324/240; 324/242
(58) Field of Classification Search .................. 324/240, 324/241, 242
See application file for complete search history.

(56) References Cited

U.S. PATENT DOCUMENTS

| | | | | |
|---|---|---|---|---|
| 4,427,940 A | * | 1/1984 | Hirama et al. | 324/240 |
| 4,495,465 A | * | 1/1985 | Tomaiuolo et al. | 324/232 |
| 4,659,991 A | * | 4/1987 | Weischedel | 324/241 |
| 6,492,808 B1 | * | 12/2002 | Sukhorukov et al. | 324/242 |

FOREIGN PATENT DOCUMENTS

| | | |
|---|---|---|
| JP | 4-151551 A | 5/1992 |
| JP | 9-210968 A | 8/1997 |
| JP | 9-274018 A | 10/1997 |
| JP | 10-19852 A | 1/1998 |
| JP | 11-230945 A | 8/1999 |
| JP | 2001-41933 A | 2/2001 |

* cited by examiner

*Primary Examiner* — Patrick Assouad
*Assistant Examiner* — David M. Schindler
(74) *Attorney, Agent, or Firm* — Buchanan Ingersoll & Rooney PC

(57) ABSTRACT

A magnetic flux generated by current excitation is allowed to pass through a part or an entire of a magnetic path of a leakage magnetic flux. A magnetic flux content due to the current excitation is temporally changed to change a leakage magnetic flux content interlinked with a detection coil so that an induced voltage is generated in the detection coil. Consequently, damage can be detected even in a case where there is no relative speed between a wire rope and a wire rope flaw detector. Further, a configuration of the magnetic path and the number of ampere turns of an exciting coil are set to be appropriate to prevent the magnetic flux generated by the current excitation from passing through the detection coil or to allow the magnetic fluxes offset each other. Thus, noise superimposition on the detection coil due to the current excitation can be prevented.

12 Claims, 12 Drawing Sheets

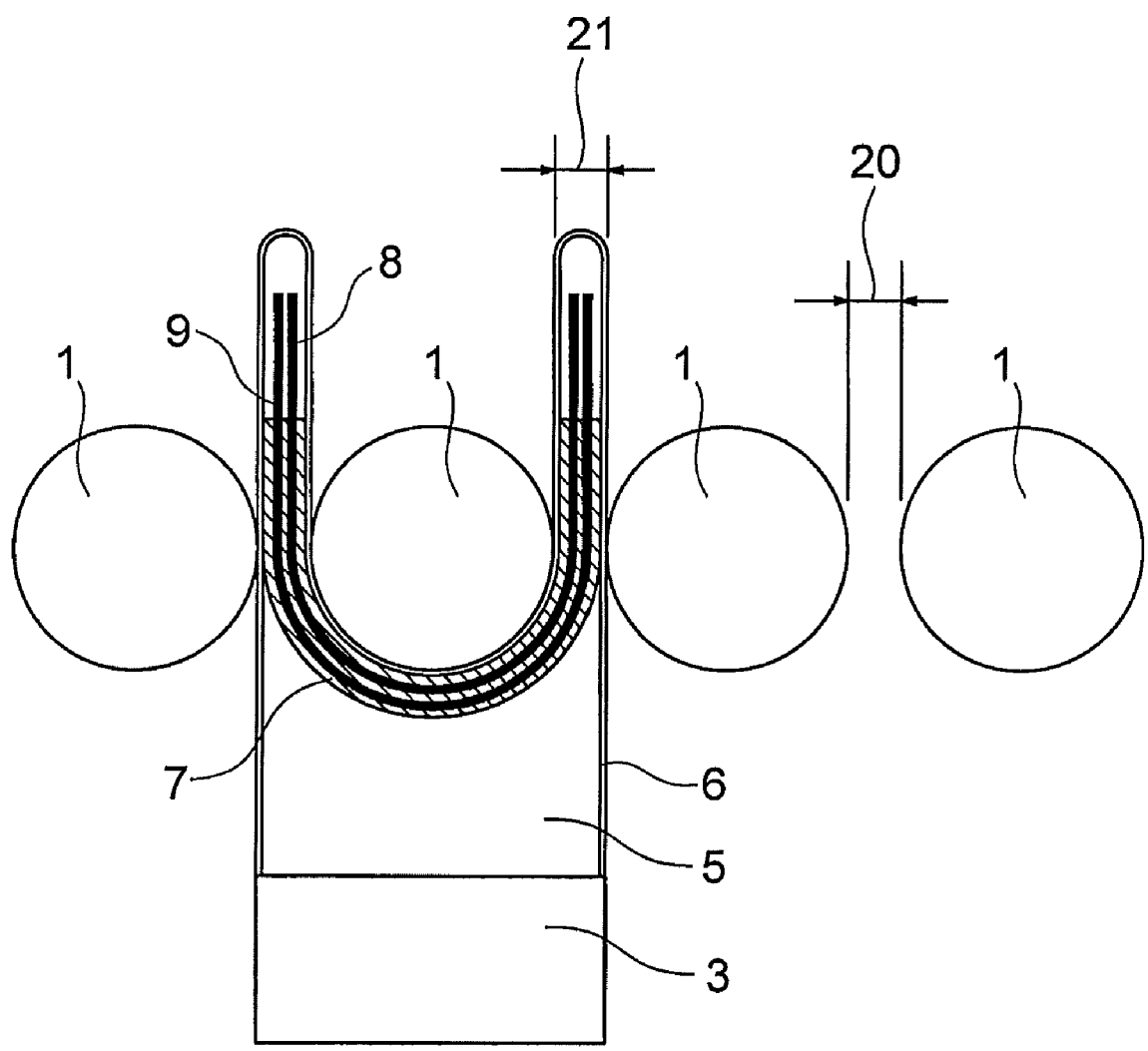

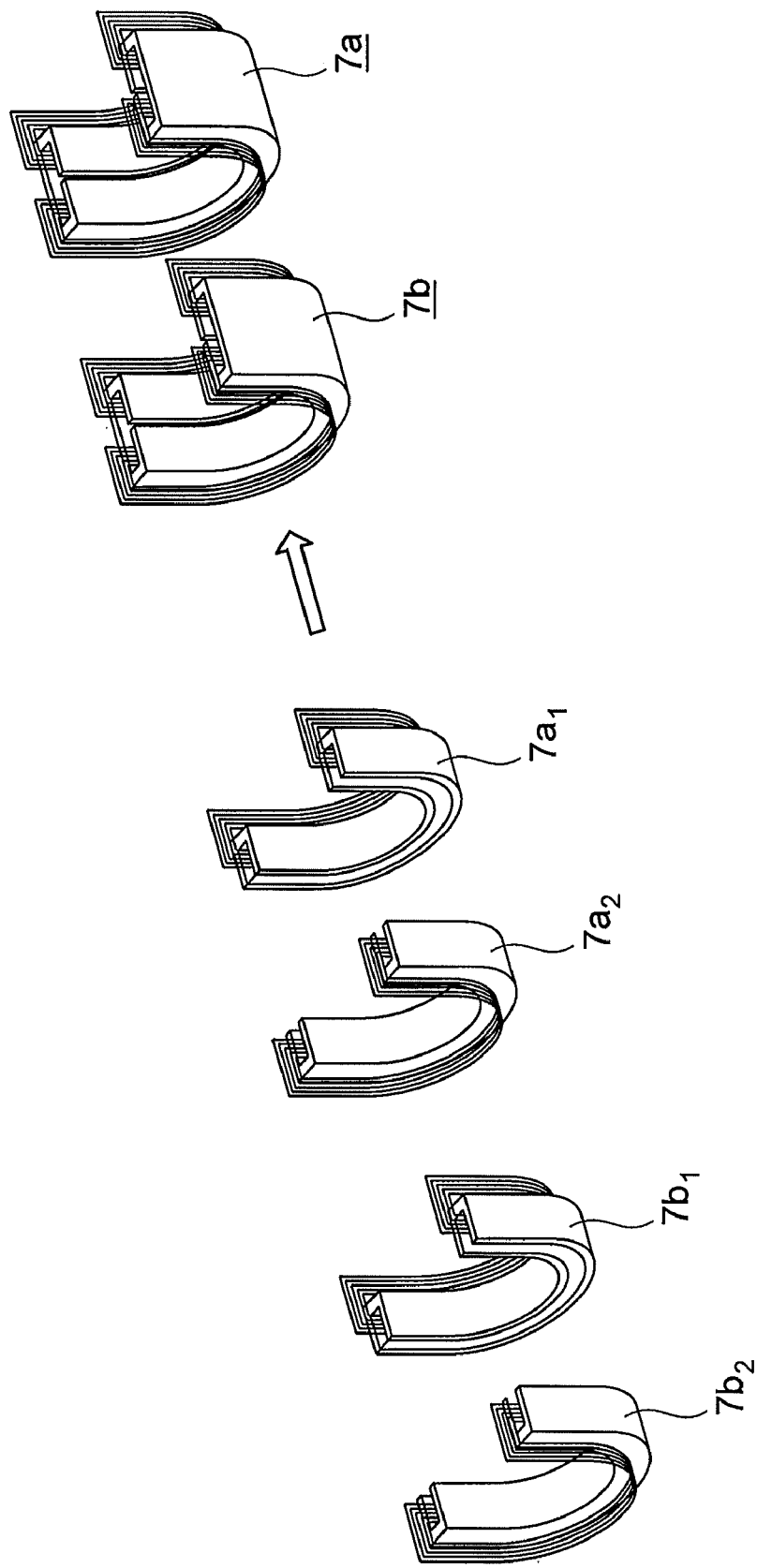

WIRE ROPE FLAW DETECTOR FOR INCREASING ACCURACY INDEPENDENT OF SPEED WHILE CONSERVING DETECTOR SIZE

TECHNICAL FIELD

The present invention relates to a wire rope flaw detector for detecting a damage of a wire rope and disconnection of a wire (hereinafter referred to as a damaged portion of the wire rope), the wire rope suspending a car of an elevator or the like.

BACKGROUND ART

A conventional wire rope flaw detector includes an exciting core having at least two magnetic poles and closely facing a wire rope, an excitation permanent magnet embedded in the exciting core, and a detection coil disposed between those two magnetic poles (for example, refer to Patent Document 1). The conventional wire rope flaw detector magnetically saturates the wire rope by the two magnetic poles to generate a leakage magnetic flux from a damaged portion such as disconnection of a wire, and detects the leakage magnetic flux by the detection coil, to thereby detect the damaged portion of the wire rope.

Further, there is another example in which an electromagnet is used to excite the wire rope to provide AC excitation (for example, refer to Patent Document 2).

Patent Document 1: JP 09-210968 A
Patent Document 2: JP 11-230945 A

DISCLOSURE OF THE INVENTION

Problems to be solved by the Invention

The wire rope flaw detector disclosed in Patent Document 1 is required to relatively move the wire rope. With the relative movement, the leakage magnetic flux moves with respect to the detection coil, and a leakage magnetic flux content interlinked with the detection coil temporally changes. Therefore, an induced voltage is generated in a detection coil terminal so as to enable the damaged portion of the wire rope to be detected. The induced voltage is proportional to a speed of the relative movement, and hence an SN ratio of a damage detection signal is improved more as the relative speed becomes larger. With appearance of such a flaw detector, an operating time of an inspector is remarkably reduced as compared with that required for conventional visual-only inspection. However, the following problems remain.

The inspector who has identified a damage signal during inspection temporarily halts the wire rope or the wire rope flaw detector for the purpose of verifying a position and the degree of damage. However, the damaged portion moves away from the wire rope flaw detector due to a time lag between the damage signal indication time and the halt time. In general, an influence of lubricating grease adhering onto a wire rope surface makes it difficult to find out a relatively small damage such as the disconnection of the wire without staring at the neighborhood of the damaged portion. Accordingly, when the damaged portion has moved away from the wire rope flaw detector, the inspector loses a marker, and cannot visually observe the damaged portion. In such a case, the inspector moves the wire rope or the wire rope flaw detector at a speed lower than the latest speed, and again searches the neighborhood of the damaged portion. However, because of the above-mentioned measurement principle, when the relative speed is smaller, the SN ratio of the damage detection signal is reduced. As a result, there arises a problem that the inspector may lose the damage depending on the degree of the damage.

On the other hand, as disclosed in Patent Document 2, there is a system in which an AC power source is used for excitation within the wire rope. In this system, the leakage magnetic flux temporally changes due to the AC excitation, and hence there is no need to relatively move the wire rope and the wire rope flaw detector. However, in order to magnetically saturate the wire rope for the purpose of bringing out the leakage magnetic flux, there is a need to cause a current corresponding to the exciting coil to flow, or to increase the number of coil turns. This leads to a problem that the wire rope flaw detector is increased in size as compared with permanent magnet excitation. Further, when an alternating magnetic flux passes within the wire rope, the magnetic flux is concentrated on a wire rope surface due to the skin effect. This leads to a problem that damage inside the wire rope cannot be detected.

The present invention has been made to solve the above-mentioned problems, and it is an object of the present invention to provide a wire rope flaw detector that is capable of obtaining a damage detection signal even when a relative speed between a wire rope and the wire rope flaw detector is small, or the relative speed is zero, and is capable of preventing the detector from increasing in size and detecting damage inside the wire rope with high precision.

Means for solving the Problems

A wire rope flaw detector according to the present invention includes: a magnetization unit that forms a main magnetic flux in a given section in an axial direction of a wire rope; and a damage detection unit that detects a damaged portion in the given section of the wire rope, in which the damage detection unit includes: a detection coil that detects a leakage magnetic flux generated by the damaged portion; an exciting coil connected to an exciting power source; and a magnetic path member made of a ferromagnetic material, around which the detection coil and the exciting coil are wound, and the exciting coil develops a magnetic flux when energized to change an interlink content of the leakage magnetic flux to the detection coil so as to develop an induced voltage in the detection coil, to thereby detect the damaged portion.

Effects of the Invention

The wire rope flaw detector according to the present invention magnetically saturates a loop magnetic path by the exciting coil so as to magnetically block a part of a bypass magnetic path. That is, a permeance of the bypass magnetic path can transition from a higher state to a lower state in a short period of time. When no leakage magnetic flux passes in the bypass magnetic path, that is, when the wire rope is not disconnected, a slight induced voltage is generated in the detection coil due to a change in the permeance of the bypass magnetic path. On the other hand, when a leakage magnetic flux passes in the bypass magnetic path, that is, when the wire rope is disconnected, the magnetic flux content in the bypass magnetic path largely changes due to a change in the permeance of the bypass magnetic path, and therefore a large induced voltage is generated in the detection coil so that the disconnection can be detected even when the relative speed between the wire rope and the wire rope flaw detector is zero. Further, the exciting coil is irrelevant to a main magnetic flux formation, and a permanent magnet can be used for the main magnetic flux formation, and hence a target to be excited by the exciting coil is limited to a loop magnetic path in the neighborhood of the bypass magnetic path, and the number of ampere turns for excitation is reduced, which prevents a magnetization unit from increasing in size. Further, the main magnetic flux does not form an alternating magnetic flux, and hence there are obtained such advantages that the skin effect can be prevented, and damage inside the wire rope can be detected with high precision.

BRIEF DESCRIPTION OF THE DRAWINGS

FIG. 8 is a view illustrating a cross section of the wire rope flaw detector according to Embodiment 1 of the present invention.

FIG. 14 is a perspective view illustrating the magnetic path member of the wire rope flaw detector according to Embodiment 3 of the present invention.

BEST MODE FOR CARRYING OUT THE INVENTION

Embodiments 1 to 3 of the present invention are described below.

Embodiment 1

Figure 1:
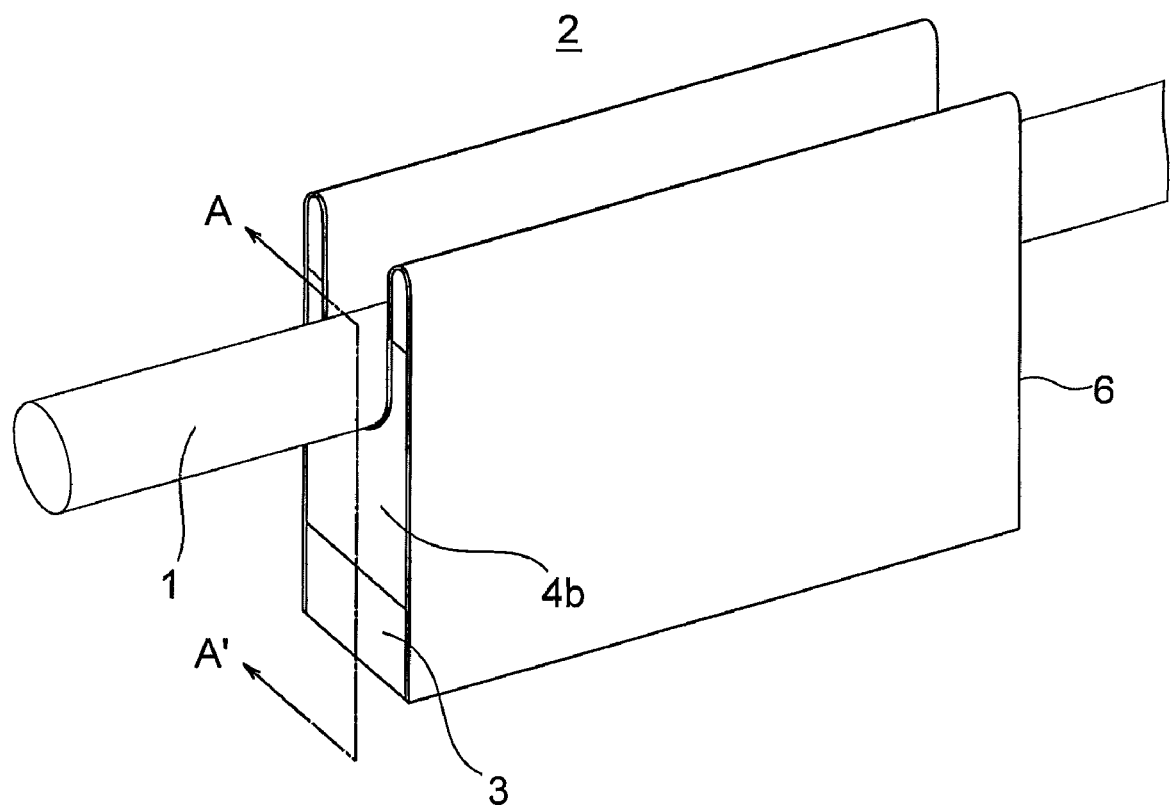
FIG. 1 is a perspective view illustrating an exterior of a wire rope flaw detector according to Embodiment 1 of the present invention.

A wire rope flaw detector according to Embodiment 1 of the present invention is described with reference to FIGS. 1 to 8. FIG. 1 is a perspective view illustrating an exterior of the wire rope flaw detector according to Embodiment 1 of the present invention. In the following description, in the respective drawings, the same symbols denote identical or corresponding parts.

In FIG. 1, a wire rope 1 and a wire rope flaw detector 2 are illustrated. Further, a back yoke 3, an excitation permanent magnet 4b, and a protecting plate 6 are illustrated.

Figure 2:
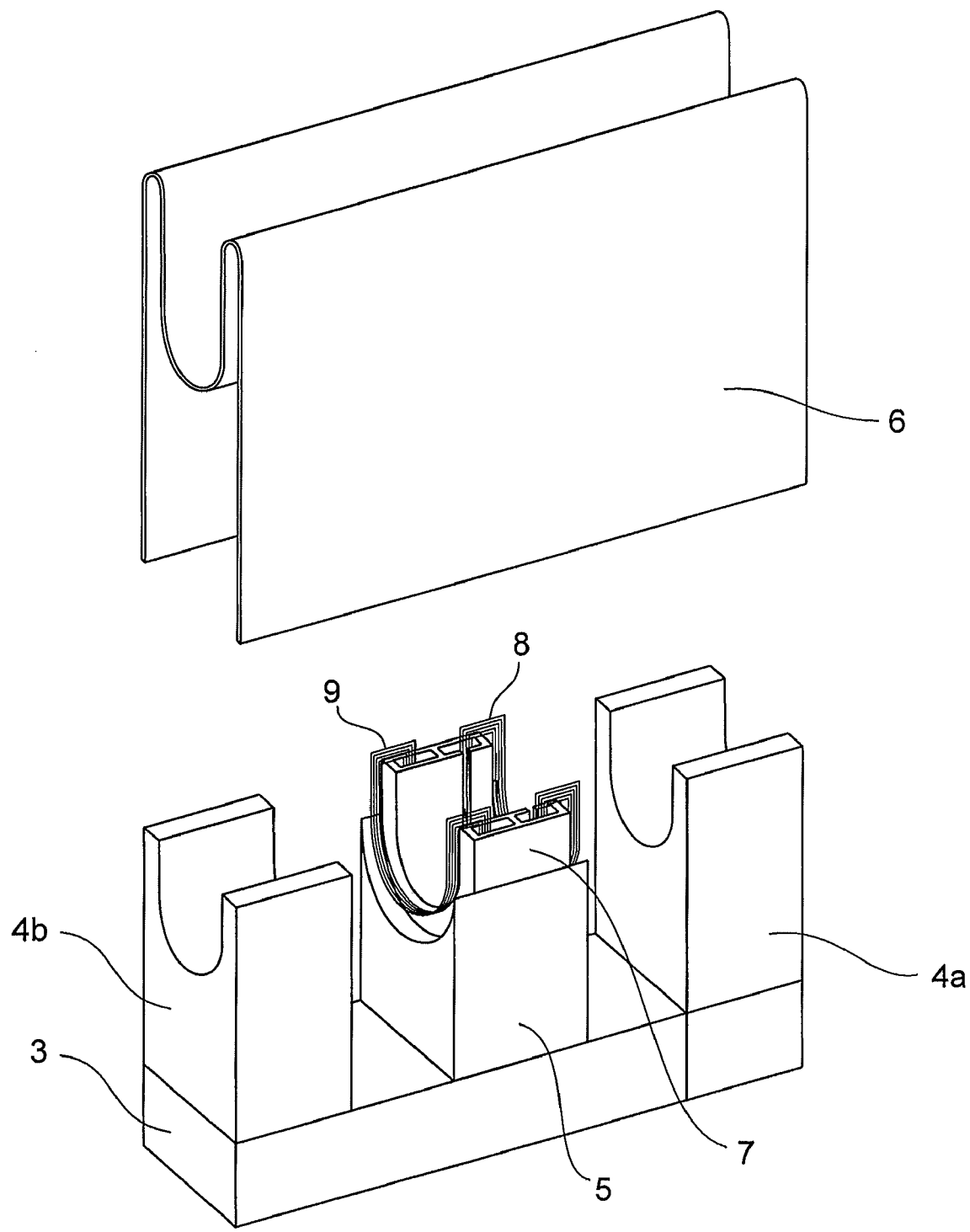
FIG. 2 is a perspective view illustrating the exterior when a protecting plate is detached from the wire rope flaw detector of FIG. 1.

FIG. 2 is a perspective view illustrating the exterior when the protecting plate is detached from the wire rope flaw detector of FIG. 1.

FIG. 2 illustrates the back yoke 3, the excitation permanent magnets 4a and 4b, a support 5, the protecting plate 6 detached from the wire rope flaw detector, a magnetic path member 7, a detection coil 8, and an exciting coil 9. A magnetization unit of the wire rope flaw detector 2 is configured to form a main magnetic path in a given section in an axial direction of the wire rope 1. The magnetization unit includes a back yoke 3 made of a ferromagnetic material such as iron, and a pair of excitation permanent magnets 4a and 4b which are disposed on both ends of the back yoke 3 with opposite polarities to each other.

Figure 3A:
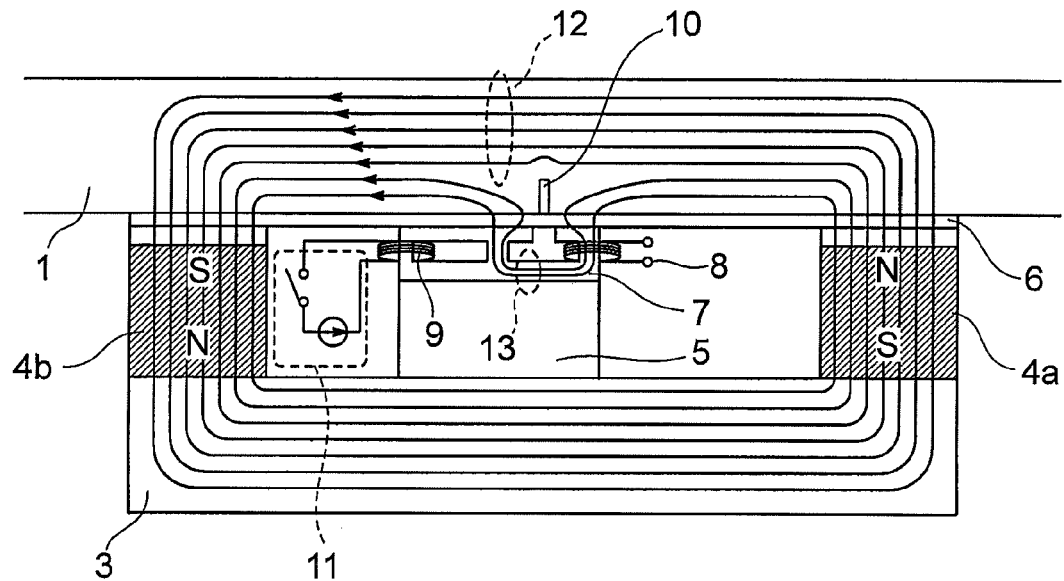
FIG. 3 are diagrams illustrating cross sections of the wire rope flaw detector taken along the line A-A' of FIG. 1.
Figure 3B:
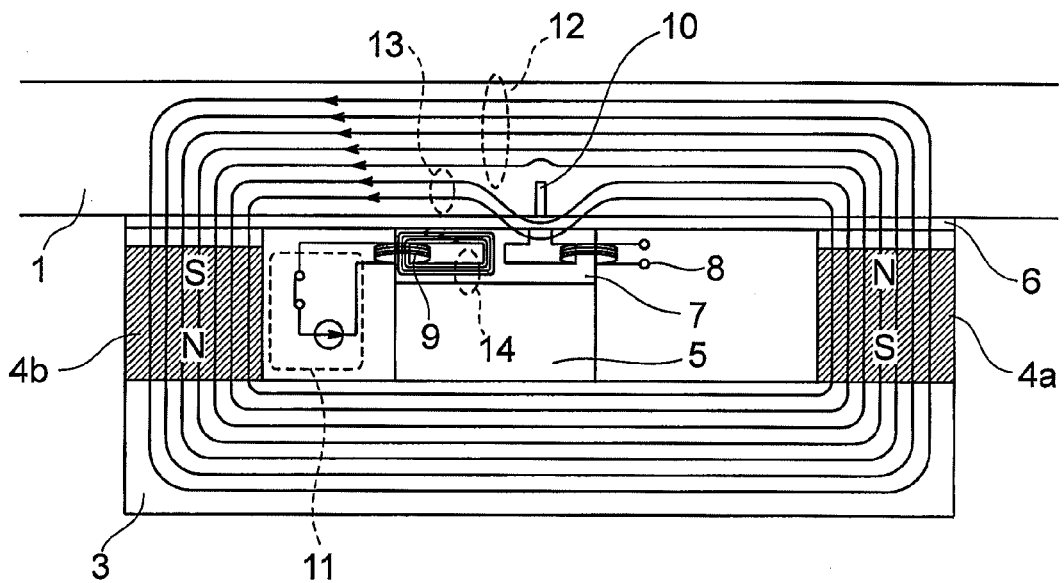

FIG. 3 are cross-sectional diagrams illustrating the wire rope flaw detector taken along the line A-A' of FIG. 1. FIG. 3 are cross-sectional diagrams taken along a plane including the central axis of the wire rope 1, illustrating a flow of magnetic flux in the vicinity of a damaged portion of the wire rope. Further, FIG. 3A illustrates a case in which no current flows in the exciting coil, and FIG. 3B illustrates a case in which a current flows in the exciting coil.

FIG. 3 illustrate the wire rope 1, the back yoke 3, the excitation permanent magnets 4a and 4b, the support 5, the magnetic path member 7, the detection coil 8, the exciting coil 9, a damaged portion 10, an exciting power source 11, a main magnetic flux 12, a leakage magnetic flux 13, and an excitation current magnetic flux 14. A damage detection unit of the wire rope flaw detector 2 includes the magnetic path member 7, the detection coil 8, the exciting coil 9, and the exciting power source 11.

Figure 4:
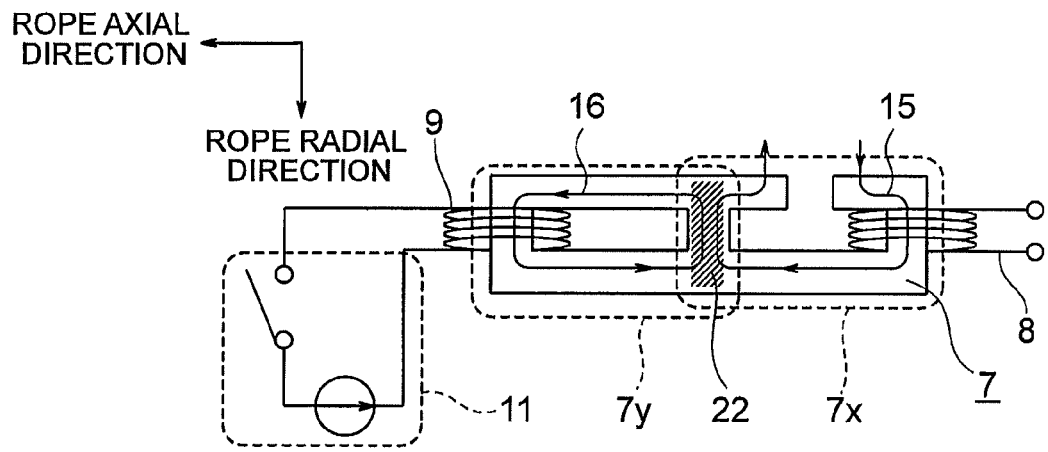
FIG. 4 is an enlarged diagram illustrating a cross section of a magnetic path member of FIG. 3.

FIG. 4 is an enlarged diagram illustrating a cross section of the magnetic path member of FIG. 3. FIG. 4 illustrates the magnetic path member 7 including a bypass magnetic path member 7x and a loop magnetic path member 7y, the detection coil 8, the exciting coil 9, the exciting power source 11, a bypass magnetic path 15 formed in the bypass magnetic path member 7x, a loop magnetic path 16 formed in the loop magnetic path member 7y, and a common portion 22 of the bypass magnetic path member 7x and the loop magnetic path member 7y.

Subsequently, an operation of the wire rope flaw detector according to Embodiment 1 is described with reference to the drawings.

The wire rope flaw detector 2 according to this embodiment forms the main magnetic path in a given section in the axial direction of the wire rope 1 by means of the magnetization unit. Further, the wire rope flaw detector 2 allows the leakage magnetic flux 13 generated by the damaged portion 10 of the wire rope 1 to go around the outside of the wire rope 1 through the magnetic path member 7, and detects the leakage magnetic flux 13 by means of the detection coil 8 wound around the bypass magnetic path member 7x of the magnetic path member 7.

FIG. 4 is the enlarged diagram illustrating the cross section of the magnetic path member 7 of FIG. 3, as described above. The magnetic path member 7 forms the bypass magnetic path 15 that allows the leakage magnetic flux to go around as well as the loop magnetic path 16. The exciting coil 9 is wound around the loop magnetic path member 7y that forms the loop magnetic path 16, and when the exciting coil 9 is energized, the loop magnetic path member 7y is magnetically saturated to deteriorate the permeability. Therefore, a part of the bypass magnetic path 15 is magnetically blocked. For that reason, the leakage magnetic flux content interlinked with the detection coil 8 is reduced to develop an induced voltage in the detection coil 8. In this way, a change in the leakage magnetic flux content interlinked with the detection coil 8 can be caused by a temporal change in the exciting coil current. Therefore, a relative speed between the wire rope 1 and the wire rope flaw detector 2 is not required, and even when the relative speed is low, the damaged portion 10 generated in the wire rope 1 can be detected with high precision.

As illustrated in FIG. 2, surfaces of the excitation permanent magnets 4a and 4b, which face the wire rope 1, each have a substantially U-shaped surface with R in which a slight margin is added to the outer diameter of the wire rope 1 and the thickness of the protecting plate 6. The reason is that an air gap (including the protecting plate 6) between each of the excitation permanent magnets 4a and 4b and the wire rope 1 is minimized to thereby effectively magnetically saturate the given section of the wire rope 1.

Figure 5:
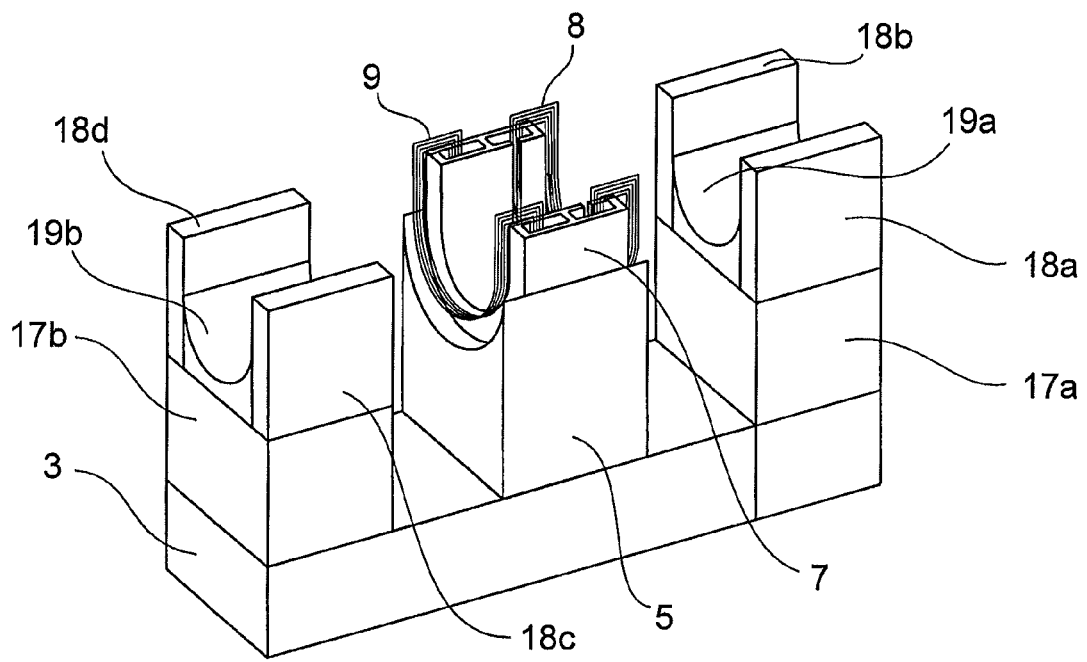
FIG. 5 is a perspective view illustrating the exterior when the protecting plate is detached from the wire rope flaw detector of FIG. 1.

FIG. 5 is a perspective view illustrating the exterior when the protecting plate is detached from the wire rope flaw detector of FIG. 1.

The excitation permanent magnet 4a may include, as illustrated in FIG. 5, a cuboid wire rope excitation main magnet 17a, cuboid wire rope excitation sub-magnets 18a and 18b, and a magnetic pole piece 19a made of a ferromagnetic material. Further, the excitation permanent magnet 4b may include, as illustrated in FIG. 5, a cuboid wire rope excitation main magnet 17b, cuboid wire rope excitation sub-magnets 18c and 18d, and a magnetic pole piece 19b made of a ferromagnetic material. As a result, because most of the permanent magnetic configuration is cuboid, the processing costs can be reduced.

The magnetic path member 7 includes the bypass magnetic path member 7x that is made of a ferromagnetic material and allows the leakage magnetic flux 13 generated by the damaged portion 10 of the wire rope 1 to go around the outside of the wire rope 1, and the loop magnetic path member 7y that contains a part of the bypass magnetic path member 7x and forms a closed loop magnetic path by itself. The magnetic path member 7 is disposed between the pair of excitation permanent magnets 4a and 4b and immediately below the protecting plate 6. Because the bypass magnetic path member 7x is made of a ferromagnetic material, the permeance of the magnetic path of the leakage magnetic flux 13 can be improved to bring out a large amount of the leakage magnetic flux 13.

Further, in a cross section of the magnetic path member 7 taken along a plane including the central axis of the wire rope 1, as illustrated in FIGS. 3 and 4, the bypass magnetic path member 7x is substantially U-shaped or substantially C-shaped, and an opening portion thereof is directed toward the wire rope 1 side. The detection coil 8 is wound around the bypass magnetic path member 7x, and the exciting coil 9 is wound around the loop magnetic path member 7y. Thus, the bypass magnetic path member 7x goes around the outside of the wire rope 1 in the substantially U-shape or the substantially C-shape so that a magnetic path length of the leakage magnetic flux 13 increases, and a winding space of the detection coil 8 increases. For that reason, the number of detection coil turns can be increased, the induced voltage generated in the detection coil 8 at the time of detecting the damaged portion 10 increases, and an SN ratio of a detection signal of the damaged portion 10 is improved.

Figure 6:
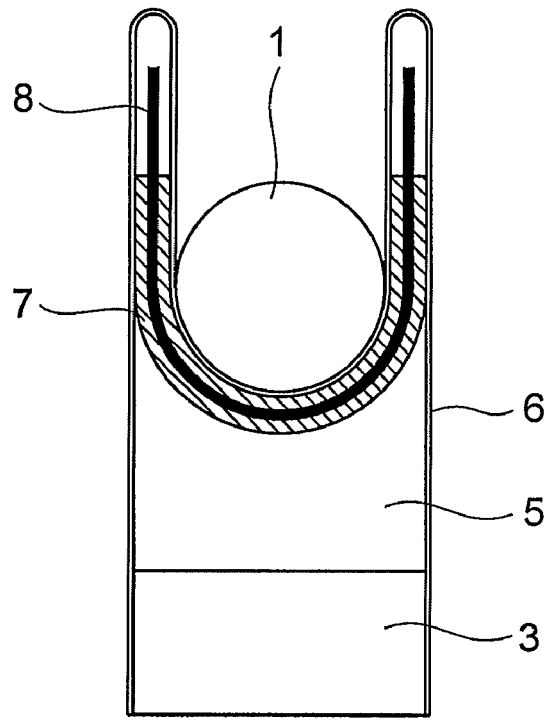
FIG. 6 is a view illustrating a cross section of the wire rope flaw detector according to Embodiment 1 of the present invention.

FIG. 6 is a cross-sectional view illustrating the wire rope flaw detector according to Embodiment 1 of the present invention. A cross section of the magnetic path member 7 taken along a plane orthogonal to the central axis of the wire rope 1 is substantially U-shaped as indicated by a shadow area of FIG. 6. This is a treatment for widening an area that can be inspected by one measurement in a circumferential direction as much as possible.

Figure 7:
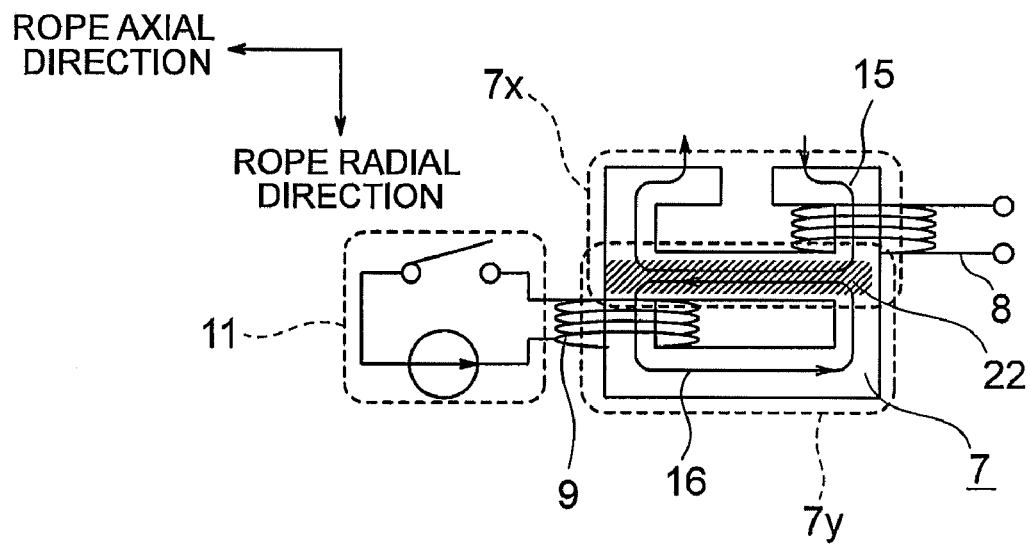
FIG. 7 is an enlarged diagram illustrating a cross section of another magnetic path member of the wire rope flaw detector according to Embodiment 1 of the present invention.

FIG. 7 is an enlarged diagram illustrating a cross section of another magnetic path member of the wire rope flaw detector according to Embodiment 1 of the present invention. As long as the loop magnetic path member 7y contains a part of the bypass magnetic path member 7x, the loop magnetic path member 7y may be disposed in the axial direction of the wire rope as illustrated in FIG. 4, or may be disposed in the radial direction of the wire rope as illustrated in FIG. 7.

However, as illustrated in FIG. 8, under the circumstances where a plurality of the wire ropes 1 are arranged in parallel in use, in the case where the wire ropes 1 are inspected, when a width thickness 21 of each U-shaped end of the wire rope flaw detector 2 is larger than a gap dimension 20 between the adjacent wire ropes, the wire rope flaw detector 2 cannot be inserted between those wire ropes 1. Accordingly, the thickness 21 of the U-shaped ends needs to be suppressed. However, because the arrangement of the loop magnetic path member 7y in the radial direction of the wire rope as illustrated in FIG. 7 increases the thickness 21 of the U-shaped ends, the arrangement in the axial direction of the wire rope illustrated in FIG. 4 is more favorable.

FIG. 3 illustrate a flow of the magnetic flux that passes through the magnetic path member 7. When the damaged portion 10 of the wire rope 1 is located in the vicinity of the opening portion of the magnetic path member 7, and when, as illustrated in FIG. 3A, no current flows in the exciting coil 9, the leakage magnetic flux 13 that has leaked from the wire rope 1 flows into one end of the bypass magnetic path member (C-type magnetic path member) 7x which is made of a ferromagnetic material, interlinks with the detection coil 8 wound around the bypass magnetic path member 7x, and returns from the other end of the bypass magnetic path member 7x to the wire rope 1.

Then, as illustrated in FIG. 3B, when a current sufficient to magnetically saturate the loop magnetic path member 7y is allowed to flow in the exciting coil 9, the common portion 22 (refer to FIG. 4) of the loop magnetic path member 7y and the bypass magnetic path member 7x is magnetically saturated, and hence the bypass magnetic path 15 is magnetically blocked. Specifically, because the permeance of the entire bypass magnetic path 15 is remarkably reduced, the leakage magnetic flux content that passes through the bypass magnetic path 15 is remarkably reduced. That is, because the magnetic flux content that interlinks with the detection coil 8 rapidly changes, an induced voltage is generated in the detection coil 8. The induced voltage of the detection coil 8 is proportional to a variation of the magnetic flux that interlinks with the detection coil 8 per unit time. Therefore, even when the exciting coil 9 operates oppositely to the above, that is, in the case where transitions are made from a state where a current flows therein to a state where the current is cut off, and the leakage magnetic flux content that passes through the bypass magnetic path 15 rapidly increases, an induced voltage reverse in positive and negative to the above-mentioned induced voltage is generated in the detection coil 8.

It is needless to say that when the wire rope 1 is not damaged, because no leakage magnetic flux 12 exists, no induced voltage is generated in the detection coil 8 regardless of whether or not a current flows in the exciting coil 9. Thus, damage occurring in the wire rope 1 can be detected even in a state where the relative speed between the wire rope 1 and the wire rope flaw detector 2 is zero.

Further, when the relative speed is not zero, a time when the leakage magnetic flux 13 passes through the bypass magnetic path 15 is limited within a period of time during which the damaged portion 10 passes through the neighborhood of the opening portion of the bypass magnetic path member 7x. However, when the exciting coil 9 is AC-excited in a cycle sufficiently shorter than the passing period of time, damage can be detected as in the static state. Further, when the relative speed is sufficiently larger, if no exciting current is allowed to flow, the disconnection of the wire can be detected by a speed electromotive force as in the conventional system. For convenience, in FIGS. 3, 4, and 7, the exciting power source 11 is represented by a current source and a switch. However, this portion may be configured by the combination of an AC power supply or a DC power supply and a semiconductor switching element.

Embodiment 2

A wire rope flaw detector according to Embodiment 2 of the present invention is described with reference to FIGS. 9 to 11. FIG. 9 are diagrams illustrating a partial configuration of the wire rope flaw detector according to Embodiment 2 of the present invention.

Figure 9A:
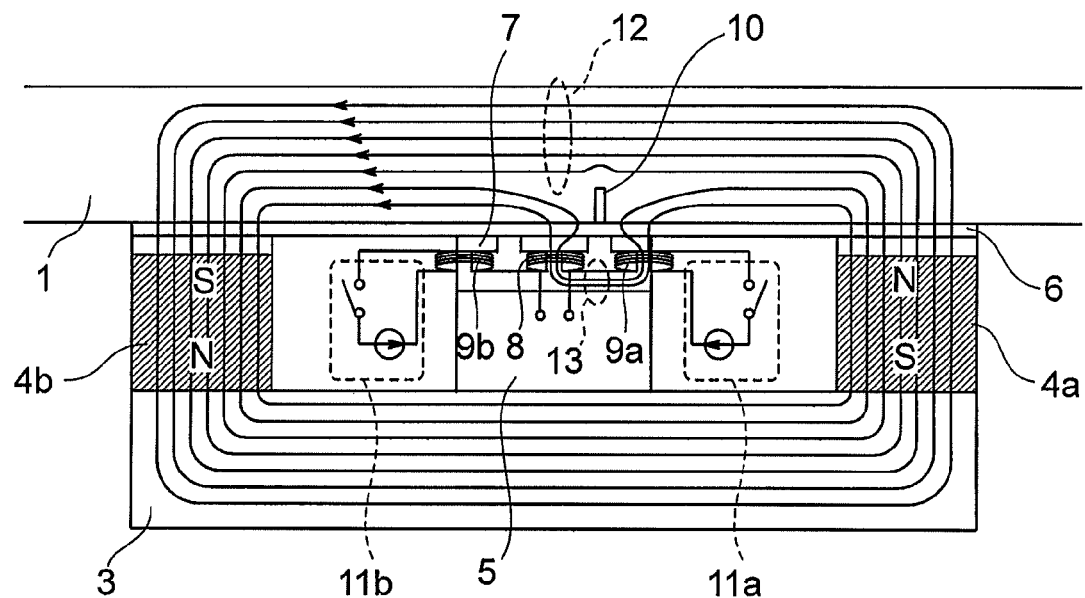
FIG. 9 are diagrams illustrating a partial configuration of a wire rope flaw detector according to Embodiment 2 of the present invention.
Figure 9B:
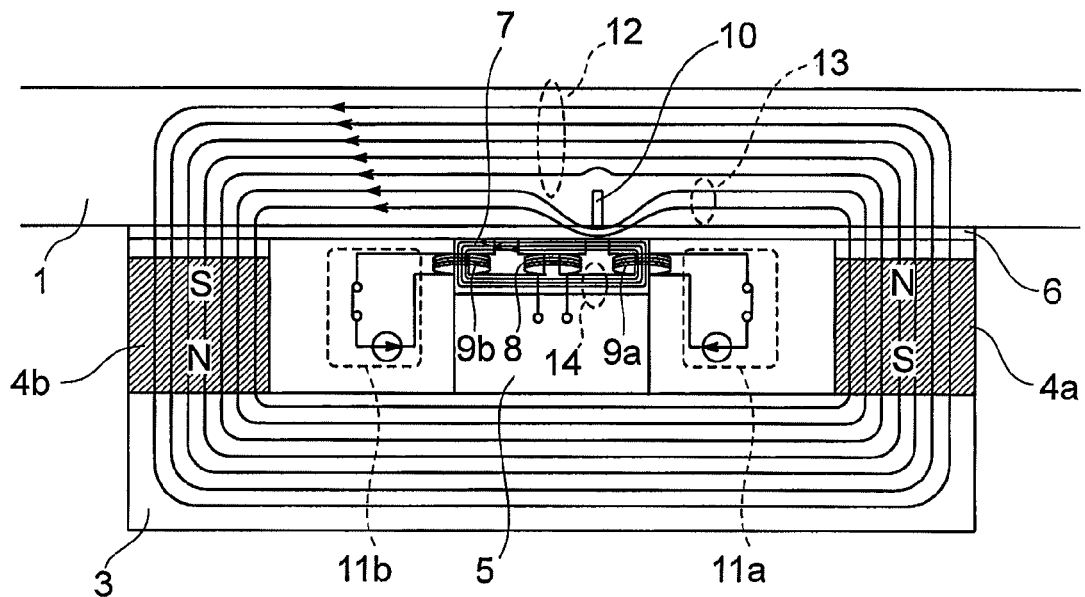

FIG. 9 are cross-sectional diagrams illustrating the wire rope flaw detector according to Embodiment 2 taken along the line A-A' of FIG. 1 like FIG. 3. FIG. 9 are cross-sectional diagrams taken along a plane including the central axis of the wire rope 1, illustrating a flow of magnetic flux in the vicinity of a damaged portion of the wire rope. Further, FIG. 9A illustrates a case in which no current flows in an exciting coil, and FIG. 9B illustrates a case in which a current flows in the exciting coil.

FIG. 9 illustrate the wire rope 1, the back yoke 3, the excitation permanent magnets 4a and 4b, the support 5, the magnetic path member 7, the detection coil 8, exciting coils 9a and 9b, the damaged portion 10, exciting power sources 11a and 11b, the main magnetic flux 12, the leakage magnetic flux 13, and the excitation current magnetic flux 14.

Figure 10:
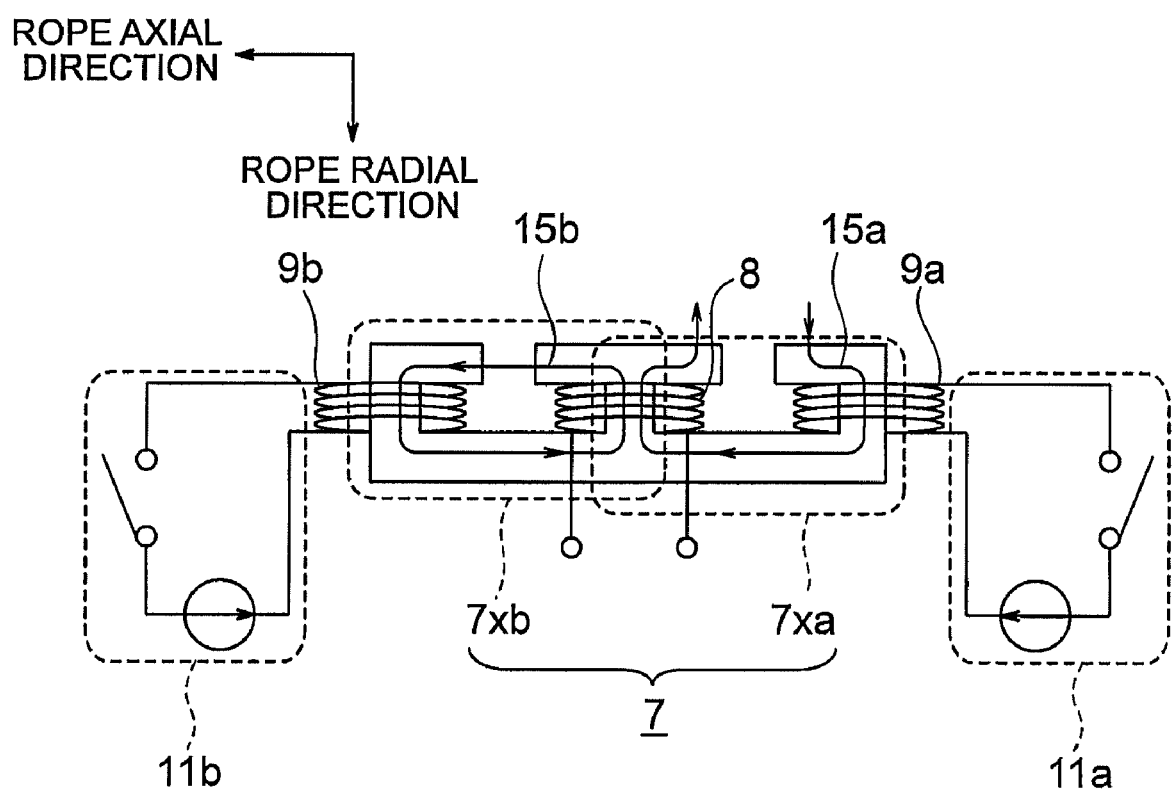
FIG. 10 is an enlarged view illustrating a cross section of a magnetic path member of FIG. 9.

FIG. 10 is an enlarged diagram illustrating a cross section of the magnetic path member of FIG. 9. FIG. 10 illustrates the magnetic path member 7 including a bypass magnetic path member 7xa and a bypass magnetic path member 7xb, the detection coil 8, the exciting coils 9a and 9b, the exciting power sources 11a and 11b, and bypass magnetic paths 15a and 15b formed in the bypass magnetic path members 7xa and 7xb.

The magnetic path member 7 according to Embodiment 2 is substantially ω-shaped or substantially E-shaped in cross section, and has the two bypass magnetic paths 15a and 15b for the leakage magnetic flux 13 as illustrated in the enlarged diagram of FIG. 10. The effect obtained by providing the substantially ω-shaped or substantially E-shaped cross-sectional configuration is identical with the effect obtained by providing the substantially ω-shaped or substantially C-shaped cross section of the bypass magnetic path member 7x of the magnetic path member 7 in Embodiment 1 described above. Further, an appearance when the magnetic path member 7 is taken along a cross section perpendicular to the axial direction of the wire rope is illustrated in FIG. 6 as in Embodiment 1 described above.

Subsequently, an operation of the wire rope flaw detector according to Embodiment 2 is described with reference to the drawings.

When the damaged portion 10 of the wire rope 1 is present in the neighborhood of any one of the two opening portions of the magnetic path member 7, if no exciting current flows, the leakage magnetic flux 13 flows in the bypass magnetic path 15a or 15b as illustrated in FIG. 9A. When the exciting coils 9a and 9b are energized, the magnetic flux 14 caused by the exciting current flows in the outer peripheral portion of the magnetic path member 7 as illustrated in FIG. 9B. The numbers of ampere turns of the exciting coils 9a and 9b are adjusted in advance so that the outer peripheral portion of the magnetic path member 7 is sufficiently saturated, and the magnetic fluxes interlinked with the detection coil 8 offset each other so as to be zero. As a result, when the exciting current flows, because the permeance of the bypass magnetic path member 15a or 15b is remarkably reduced, the leakage magnetic flux content that passes through the bypass magnetic paths 15a and 15b is remarkably reduced. As a result, because the magnetic flux content interlinked with the detection coil 8 rapidly changes, an induced voltage is generated in the detection coil 8, and the damaged portion 10 can be detected.

Further, as in Embodiment 1 described above, even when transitions are made from a state in which the exciting current flows to a state in which no exciting current flows, and the leakage magnetic flux content that passes through the bypass magnetic paths 15a and 15b rapidly increases, an induced voltage reverse in positive and negative to the above-mentioned induced voltage is generated in the detection coil 8. Further, when there is no damage, no induced voltage is generated in the detection coil 8 regardless of whether or not a current flows in the exciting coils 9a and 9b.

The advantage of Embodiment 2 resides in that the two bypass magnetic paths 15a and 15b are provided. It is assumed that when the damaged portion 10 existing on the wire rope 1 is present in the neighborhood of the opening portion of the bypass magnetic path member 7xa, an induced voltage having a phase shifted by θ° with respect to the exciting current is generated in the detection coil 8. Then, when the damaged portion 10 moves up to the opening portion of the bypass magnetic path member 7xb by a given distance, the polarity of the leakage magnetic flux that passes through the detection coil 8 is reversed, and hence the induced voltage generated in the detection coil 8 is shifted in phase with respect to the exciting current by $(\theta+180)°$. That is, when the wire rope 1 and the wire rope flaw detector 2 have a given positional relationship, and an induced voltage is generated in the detection coil 8, if the induced voltage is caused by damage, the wire rope flaw detector 2 is displaced from the positional relationship by a given distance so that the induced voltage reversed in phase can be identified. However, when the cause of the generated voltage is the other noise (such as noise caused by vibration of the wire rope 1), such an induced voltage cannot be identified, and hence the reliability of the detection of the damaged portion 10 can be improved.

Figure 11:
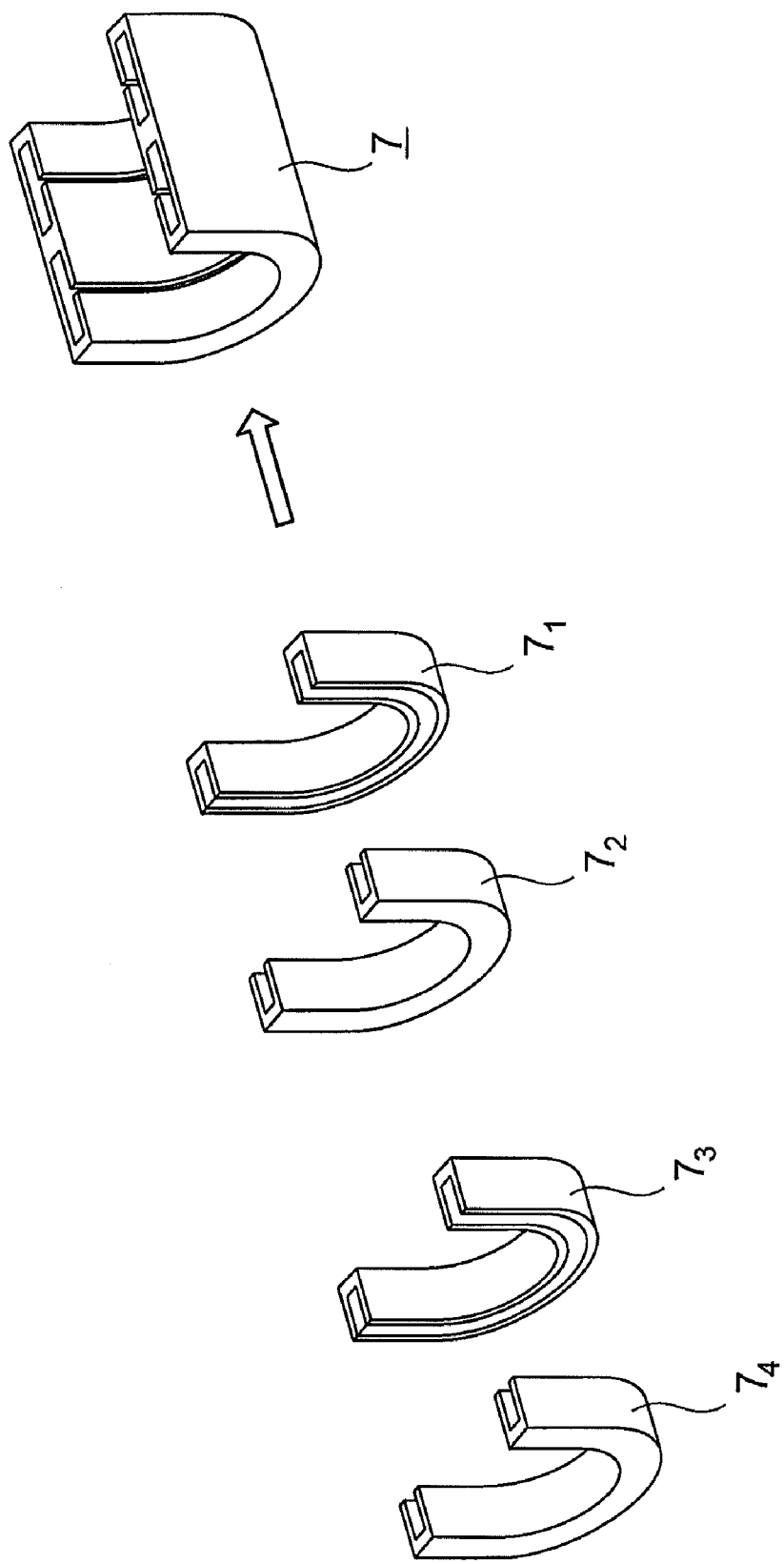
FIG. 11 is a perspective view illustrating the magnetic path member of the wire rope flaw detector according to Embodiment 2 of the present invention.

Further, the magnetic path member 7 used in Embodiment 2 can be fabricated by sticking four magnetic materials $7_1$, $7_2$, $7_3$, and $7_4$ having the same configuration together as illustrated in FIG. 11, which contributes to standardization of parts and the reduced manufacture costs.

Embodiment 3

A wire rope flaw detector according to Embodiment 3 of the present invention is described with reference to FIGS. 12 to 14. FIG. 12 are diagrams illustrating a partial configuration of the wire rope flaw detector according to Embodiment 3 of the present invention.

Figure 12A:
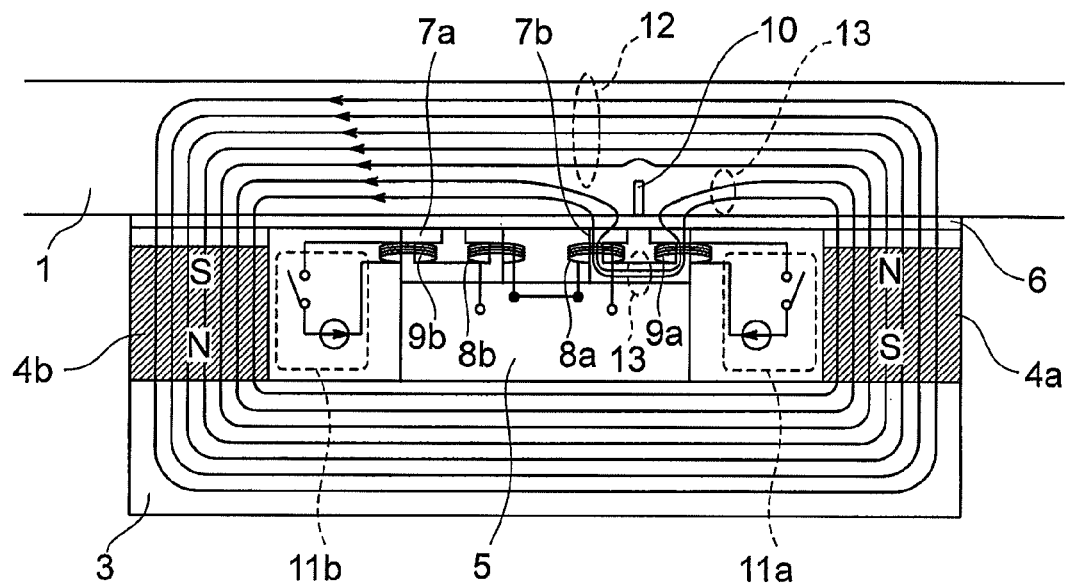
FIG. 12 are diagrams illustrating a partial configuration of a wire rope flaw detector according to Embodiment 3 of the present invention.
Figure 12B:
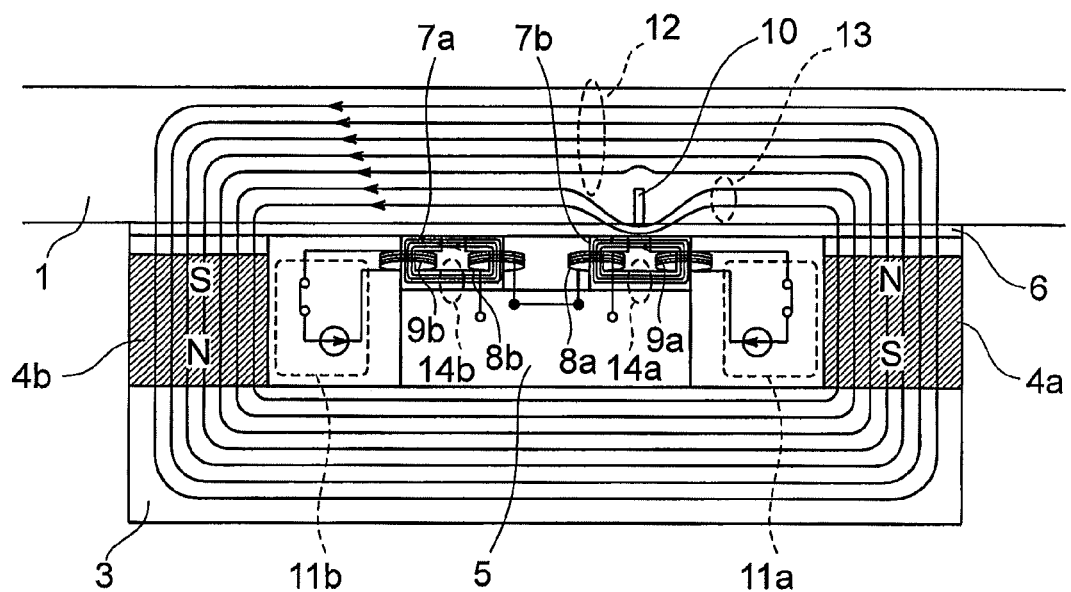

FIG. 12 are cross-sectional diagrams illustrating the wire rope flaw detector according to Embodiment 3 taken along the line A-A' of FIG. 1 like FIG. 3. FIG. 12 are cross-sectional diagrams taken along a plane including the central axis of the wire rope 1, illustrating a flow of magnetic flux in the vicinity of a damaged portion of the wire rope. Further, FIG. 12A illustrates a case in which no current flows in an exciting coil, and FIG. 12B illustrates a case in which a current flows in the exciting coil.

FIG. 12 illustrate the wire rope 1, the back yoke 3, the excitation permanent magnets 4a and 4b, the support 5, magnetic path members 7a and 7b, detection coils 8a and 8b, the exciting coils 9a and 9b, the damaged portion 10, the exciting power sources 11a and 11b, the main magnetic flux 12, the leakage magnetic flux 13, and excitation current magnetic fluxes 14a and 14b.

Figure 13:
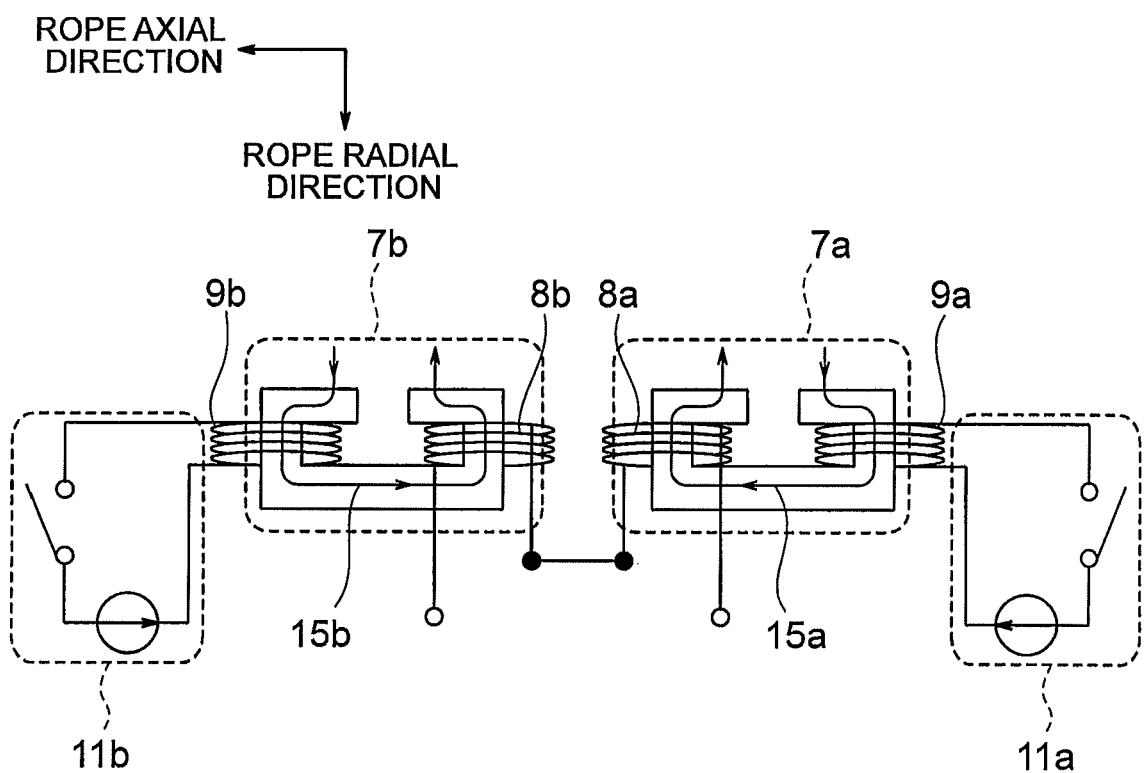
FIG. 13 is an enlarged diagram illustrating a cross section of a magnetic path member of FIG. 12.

FIG. 13 is an enlarged diagram illustrating a cross section of the magnetic path members of FIG. 12. FIG. 13 illustrates the magnetic path members 7a and 7b, the detection coils 8a and 8b, the exciting coils 9a and 9b, the exciting power sources 11a and 11b, and the bypass magnetic paths 15a and 15b.

The magnetic path member according to Embodiment 3 includes the two magnetic path members 7a and 7b that are substantially U-shaped or substantially C-shaped in cross section, and no common portion of the two bypass magnetic path members exists. The effect obtained by providing the substantially U-shaped or substantially C-shaped cross-sectional configuration of the magnetic path members 7a and 7b is identical with the effect in Embodiment 1 described above.

Subsequently, an operation of the wire rope flaw detector according to Embodiment 3 is described with reference to the drawings.

The detection coils 8a and 8b and the exciting coils 9a and 9b are wound around the magnetic path members 7a and 7b, respectively, as illustrated in FIGS. 12 and 13. The detection coils 8a and 8b are identical in winding direction with respect to the wire rope 1 (unified dextrorsely or sinistrorsely viewed from the wire rope 1 side), and one winding start terminal and the other winding end terminal are connected in series. When the exciting current flows, the magnetic fluxes 14a and 14b caused by the exciting current independently flow in the respective bypass magnetic paths 15a and 15b formed in the magnetic path members 7a and 7b. When the numbers of ampere turns of the exciting currents are adjusted in advance so that the induced voltages generated in the detection coils 8a and 8b offset each other so as to be zero, the same function as that in Embodiment 2 described above can be obtained.

According to Embodiment 3, as illustrated in FIG. 14, magnetic path members $7a_1$, $7a_2$, $7b_1$, and $7b_2$, and standardized assemblies 7a and 7b of the coil can be combined together for fabrication, which contributes to standardization of parts and processes and the reduced manufacturing costs.

The invention claimed is:

1. A wire rope flaw detector, comprising:
   a magnetization unit that forms a main magnetic flux in a given section in an axial direction of a wire rope; and
   a damage detection unit that detects a damaged portion in the given section of the wire rope,
   wherein the damage detection unit comprises:
   a detection coil that detects a leakage magnetic flux generated by the damaged portion;
   an exciting coil connected to an exciting power source; and
   a magnetic path member made of a ferromagnetic material, around which the detection coil and the exciting coil are wound, wherein the magnetic path member comprises:
   a bypass magnetic path member around which the detection coil is wound; and a loop magnetic path member that shares a common portion with the bypass magnetic path member, said loop magnetic path member being wound with the exciting coil, and
   wherein the exciting coil develops a magnetic flux when energized to modify the common portion to inversely change the amount of leakage magnetic flux in the detection coil so as to develop an induced voltage in the detection coil, to thereby detect the damaged portion.

2. A wire rope flaw detector according to claim 1, wherein the bypass magnetic path member has a substantially U-shaped or substantially C-shaped cross section taken along a plane including a central axis of the wire rope, and wherein the bypass magnetic path member has a substantially U-shaped or substantially C-shaped opening portion to accommodate the wire rope.

3. A wire rope flaw detector according to claim 2, wherein the magnetic path member has a substantially U-shaped cross section taken along a plane orthogonal to the central axis of the wire rope, so as to at least partially surround the wire rope in a circumferential direction.

4. A wire rope flaw detector according to claim 3, wherein the loop magnetic path member forms therein a loop magnetic path coupled with a bypass magnetic path formed in the bypass magnetic path member in the axial direction of the wire rope.

5. A wire rope flaw detector according to claim 3, wherein the loop magnetic path member forms therein a loop magnetic path coupled with a bypass magnetic path formed in the bypass magnetic path member in a radial direction of the wire rope.

6. A wire rope flaw detector according to claim 1, wherein the modification of the common portion is a change in permeability of the common portion.

7. A wire rope flaw detector comprising:
   a magnetization unit that forms a main magnetic flux in a given section in an axial direction of a wire rope; and
   a damage detection unit that detects a damaged portion in the given section of the wire rope,
   wherein the damage detection unit comprises:
   a magnetic path member made of a ferromagnetic material, and which comprises:
   a first bypass magnetic path member, and
   a second bypass magnetic path member that shares a common portion with the first bypass magnetic path member,
   a first exciting coil connected to a first exciting power source, said first exciting coil being wound around said first bypass magnetic path member to form a first bypass magnetic path;
   a second exciting coil connected to a second exciting power source, said second exciting coil being wound around said second bypass magnetic path member to form a second bypass magnetic path; and
   a detection coil wound around the common portion to detect a leakage magnetic flux generated by the damaged portion
   wherein the first bypass magnetic path and the second bypass magnetic path are coupled with each other in the axial direction of the wire rope, and are formed magnetically symmetrically with respect to the common portion, and
   wherein the exciting coils develop a magnetic flux when energized to modify the common portion to inversely change the amount of leakage magnetic flux in the detection coil so as to develop an induced voltage in the detection coil, to thereby detect the damaged portion.

8. A wire rope flaw detector according to claim 7, wherein the magnetic path member has a substantially w-shaped or substantially E-shaped cross section taken along a plane including a central axis of the wire rope, and
   wherein the magnetic path member has a substantially w-shaped or substantially E-shaped opening portion directed toward the wire rope.

9. A wire rope flaw detector according to claim 8, wherein the magnetic path member has a substantially U-shaped cross section taken along a plane orthogonal to the central axis of the wire rope, so as to at least partially surround the wire rope in a circumferential direction.

10. A wire rope flaw detector comprising:
a magnetization unit that forms a main magnetic flux in a given section in an axial direction of a wire rope; and
a damage detection unit that detects a damaged portion in the given section of the wire rope,
wherein the damage detection unit comprises:
a magnetic path member made of a ferromagnetic material, and which comprises:
　a first bypass magnetic path member, and
　a second bypass magnetic path member,
　wherein the first bypass magnetic path member and the second bypass magnetic path member are separated from each other, and disposed in the axial direction of the wire rope, and
a first exciting coil connected to a first exciting power source, said first exciting coil being wound around said first bypass magnetic path member;
a second exciting coil connected to a second exciting power source, said second exciting coil being wound around said second bypass magnetic path member;
a first detection coil wound around said first bypass magnetic path member; and
a second detection coil wound around said second bypass magnetic path member;
wherein the first detection coil and the second detection coil are connected in series, and
wherein the exciting coils develop a magnetic flux when energized to inversely change the amount of leakage magnetic flux in the detection coils so as to develop an induced voltage in the detection coils, to thereby detect the damaged portion.

11. A wire rope flaw detector according to claim 10, wherein each of the first magnetic path member and the second magnetic path member has a substantially U-shaped or substantially C-shaped cross section taken along a plane including a central axis of the wire rope, and
　wherein the each of the first magnetic path member and the second magnetic path member has a substantially U-shaped or substantially C-shaped opening portion directed toward the wire rope.

12. A wire rope flaw detector according to claim 11, wherein the magnetic path member has a substantially U-shaped cross section taken along a plane orthogonal to the central axis of the wire rope, so as to at least partially surround the wire rope in a circumferential direction.

* * * * *